United States Patent
Kirsch et al.

(10) Patent No.: US 6,553,326 B1
(45) Date of Patent: Apr. 22, 2003

(54) ERRORS IN SYSTEMS USING MAGNETIC FIELDS TO LOCATE OBJECTS

(75) Inventors: Stefan R. Kirsch, Lauchringen (DE); Christian J. Schilling, Wuerenlingen (CH)

(73) Assignee: Northern Digital Inc., Waterloo (CA)

( * ) Notice: Subject to any disclaimer, the term of this patent is extended or adjusted under 35 U.S.C. 154(b) by 0 days.

(21) Appl. No.: 09/544,539

(22) Filed: Apr. 7, 2000

(51) Int. Cl.[7] ............................. A61B 5/05; G01B 7/14
(52) U.S. Cl. .................. 702/65; 324/207.17; 324/318; 324/345; 600/407; 600/424
(58) Field of Search .......................... 702/36, 38, 57, 702/72, 65, 84, 153; 324/207.12, 207.17, 248, 318, 345; 600/407, 424

(56) References Cited

U.S. PATENT DOCUMENTS

| | | | |
|---|---|---|---|
| 5,392,210 A | 2/1995 | Scholz | 324/248 |
| 5,457,641 A | 10/1995 | Zimmer | 702/153 |
| 5,572,132 A * | 11/1996 | Pulyer et al. | 324/318 |
| 5,629,626 A * | 5/1997 | Russell et al. | 324/345 |
| 5,747,996 A | 5/1998 | Fuchs | 324/207.17 |
| 5,752,513 A * | 5/1998 | Acket et al. | 600/424 |
| 5,762,064 A | 6/1998 | Polvani | 600/424 |
| 5,767,669 A | 6/1998 | Hansen et al. | 324/207.12 |
| 5,879,297 A | 3/1999 | Haynor | 600/407 |
| 5,913,820 A | 6/1999 | Bladen | 600/407 |
| 6,073,043 A | 6/2000 | Schneider | 600/424 |
| 6,211,666 B1 * | 4/2001 | Acker | 324/207.17 |
| 6,263,230 B1 * | 7/2001 | Haynor et al. | 600/424 |
| 6,369,564 B1 * | 4/2002 | Khalfin et al. | 324/207.17 |

FOREIGN PATENT DOCUMENTS

| | | | |
|---|---|---|---|
| GB | 2331807 | 6/1999 | A61B/5/06 |
| WO | WO9736192 | 10/1997 | G01V/15/00 |

* cited by examiner

Primary Examiner—John Barlow
Assistant Examiner—John Le
(74) Attorney, Agent, or Firm—Fish & Richardson P.C.

(57) ABSTRACT

A process detects distortions to magnetic location or orientation determinations. The process includes measuring a plurality of magnetic field values, determining one of a probe's location and a probe's orientation from an extremum of an optimization function. The measured values depend on the probe's location and orientation. The optimization function depends on the measured field values and field values calculated from a model. The process also includes indicating that a distortion to the determining exists in response to the extremum belonging to a preselected range.

27 Claims, 8 Drawing Sheets

Fig. 8 ize_ref>

ERRORS IN SYSTEMS USING MAGNETIC FIELDS TO LOCATE OBJECTS

TECHNICAL FIELD

This invention relates to systems that use magnetic fields to determine an object's location and orientation.

BACKGROUND

As is known in the art, systems may use magnetic fields to determine the location and orientation of an object. Such systems use magnetic field measurements to indirectly determine the location and orientation of the object. These systems are useful, for example, in the medical field, because they are able to accurately locate an object in a patient's body with only minimal intrusion into the body. The intrusion involves placing a small probe near the object to be located. Then, the 3-dimensional location and orientation of the probe is determined from the effect that the probe's location and orientation have on magnetic field measurements.

The probe may be either a source or a sensor of a magnetic field. If the probe is a source, sensors exterior to the body measure the field produced by the probe. If the probe is a sensor, magnetic sources exterior to the body produce the fields being measured.

A common feature of systems that use magnetic field measurements to determine a probe's location and orientation is that measured magnetic fields are nonlinear functions of the location and orientation. Due to the non-linearity, an iterative process is used to determine the probe's location and orientation from the measured magnetic field values. The iterative process compares values of the magnetic field for guessed probe locations and orientations to the measured values. If the field values at a guessed location and orientation are close to the measured values, the guessed and actual probe locations and orientations are also close.

The iterative process uses a physical model for the probe's environment. The physical model specifies the location and orientation of each field source. From the specified locations and orientations, laws of electrodynamics determine the field values.

SUMMARY

In a first aspect, the invention features a process for detecting distortions to probe location or orientation determinations. The process includes measuring a plurality of magnetic field values, determining one of a probe's location and a probe's orientation from an extremum of an optimization function. The measured values depend on the probe's location and orientation. The optimization function depends on the measured field values and a model for the measured field values. The process also includes indicating that a distortion to the act of determining exists in response to the extremum belonging to a preselected set.

In a second aspect, the invention features a system for magnetically locating a probe. The system includes a plurality of magnetic field sensors or sources, a probe, and a processor coupled to receive the measured values. The probe's location and orientation affects measured magnetic field values. The processor detects either a system failure or a field distortion from a value of an optimization function. The optimization function depends on differences between the measured field values and field values predicted from a physical model.

In a third aspect, the invention features a calibration process. The process includes setting up a condition that distorts determinations of a probe's location and orientation from measured field values, determining an actual probe location and orientation, and measuring magnetic field values that depend on the location and orientation. The process also includes finding an extremum of an optimization function and labeling the extremum as a value indicative of the condition. The optimization function depends on differences between the measured field values and field values calculated from a guessed probe location and position.

In a fourth aspect, the invention features a process. The process includes measuring a plurality of magnetic field values, estimating a location and orientation of a probe, and calculating magnetic field values for the estimated location and orientation. The measured field values are functions of the location and orientation of the probe. The process also includes determining a value of an error function that depends on differences between the measured and calculated field values and determining whether a distortion of the measured values has occurred from the value of the error function.

In a fifth aspect, the invention features a program storage device storing a computer executable program of instructions to perform one of the above-described processes.

Other features and advantages of the invention will be apparent from the description, drawings, and claims.

DETAILED DESCRIPTION MAGNETIC LOCATION MEASUREMENT SYSTEMS

Figure 1:
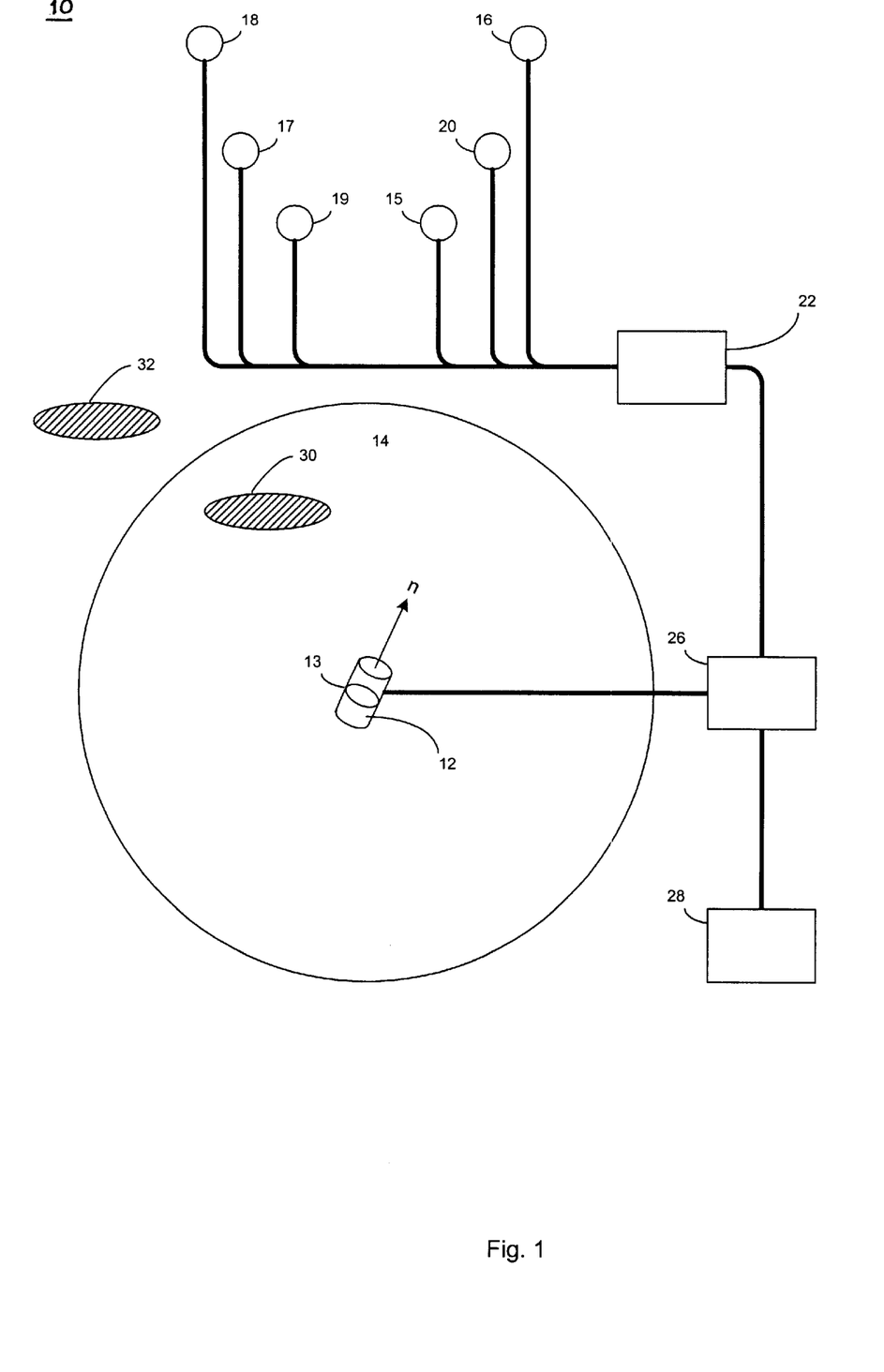
FIG. 1 is a schematic view of a system that uses magnetic measurements to find a probe's location and orientation.

FIG. 1 is a schematic view of a system 10 that uses measurements of magnetic fields to find the location and orientation of a moveable probe 12. The moveable probe 12 is located inside a volume 14, e.g., a body of a medical patient. The system 10 also includes a plurality of field sources 15–20, e.g., small induction coils, which are located outside of the volume 14. Other embodiments may place the field sources 15–20 around the volume 14 in which the probe 12 is located. The field sources 15–20 are driven by a field-generating module 22, e.g., an alternating or direct current source.

Figure 2:
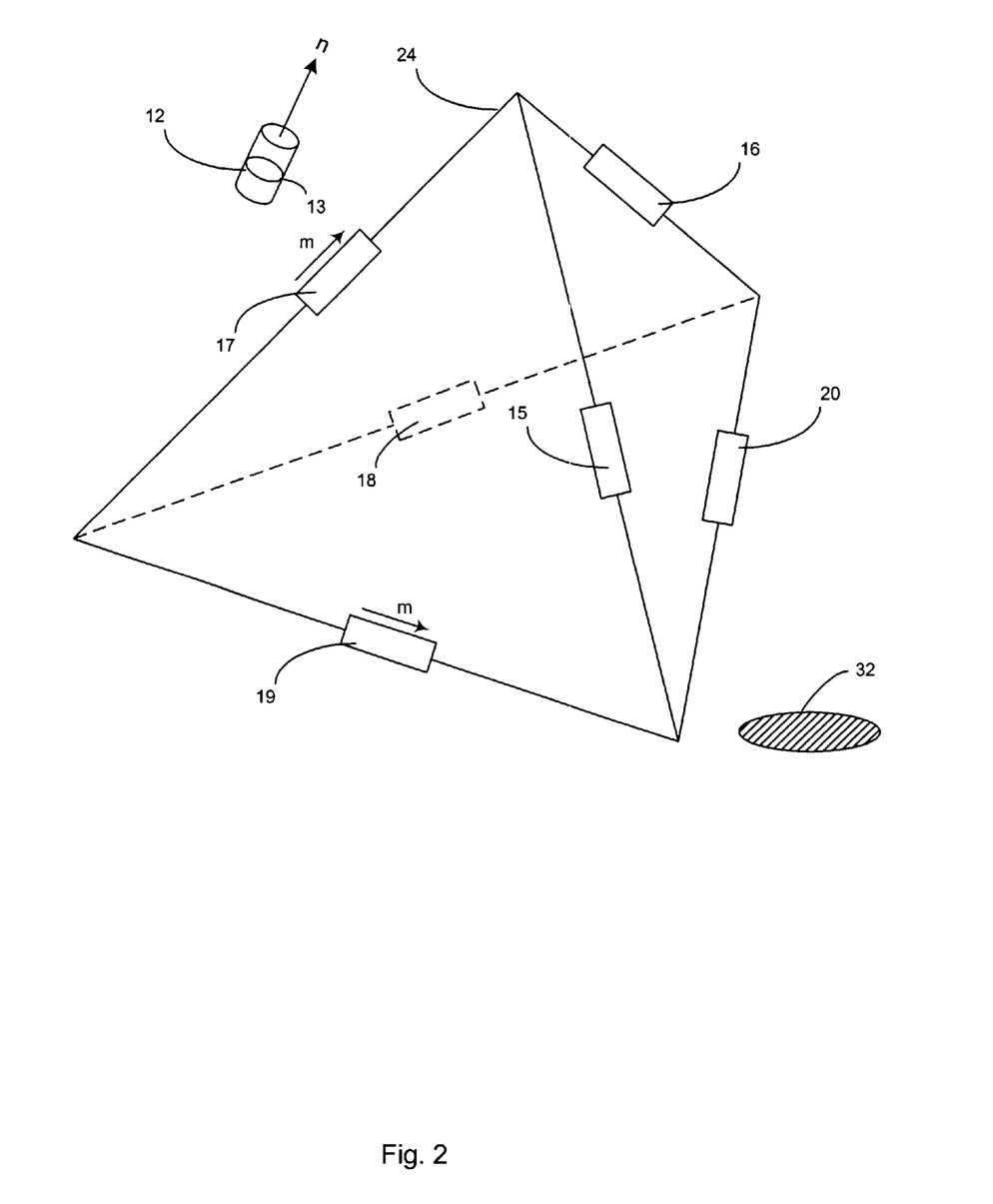
FIG. 2 is a side view of the system of FIG. 1.

FIG. 2 is a side view of the system 10 that shows orientations and locations of the field sources 15–20 and probe 12 in 3-dimensions. Each field source 15–20 is located at the center of an edge of a regular tetrahedron 24. The field sources 15–20 are oriented so that their internal magnetic moments "m" are parallel to the edges of a tetrahedron 24. The probe 12 is located outside the tetrahedron 24 and has an orientation defined by a normal direction "n" to a sensor 13 that measures local magnetic field values. The sensor 13 may include a simple coil, several coils, a Hall sensor, or a flux gate sensor and may measure a magnetic field flux or magnetic field differential.

Each source 15–20 may also include a single or multiple field coils. For a source 15–20 with a single coil, the magnetic field in the volume 14 is a dipole field. For a source 15–20 with several coils, the magnetic field in the volume 14 may be a higher multipole field. In one embodiment, each source 15–20 uses two identical coils whose normal vectors are anti-parallel. Such a source produces a magnetic quadrupole field in the volume 14. A quadrupole field has larger spatial variations than a dipole field and thus, may be more convenient for locating probe 12.

Other embodiments may use field sources 15–20 that primarily generate higher magnetic multipole fields.

Other embodiments may use different numbers of field sources 15–20 or locate and orient the field sources 15–20 differently.

Referring to FIGS. 1 and 2, magnetic fields from the sources 15–20 induce electromotive forces (EMF's) in an internal sensor coil 13 of the probe. The EMF's are measured by an electronics module 26 that connects to the probe 12. By measuring EMF's, the electronics module 26 measures local values of magnetic fields at the probe's location and orientation 12. The electronics module 26 also can identify the individual source 15–20 that produces each measured EMF's.

In one embodiment, measurement timing information is used to identify the source 15–20 producing a measured field. In this embodiment, the field-generating module 22 temporally multiplexes power to the different field sources 15–20 and relays timing information to the electronics module 26.

In another embodiment, the field generating 22 drives each field source 15–20 at a different frequency. To identify the particular source 15–20 of a measured field, the electronics module 26 or a computer 28 decomposes measured EMF's from the probe's coil 13 into frequency components. Frequency components of the measured fields are matched to individual field sources 15–20.

In either embodiment, electronics module 26 outputs several measured magnetic fields, $B_1^{measured}$ to $B_6^{measured}$, corresponding to individual field sources 15–20. The measured magnetic field values, $B_1^{measured}$ to $B_6^{measured}$, depend on the 3-dimensional location and the orientation of the probe's coil 13.

The electronics module 26 sends the measured field values to a computer 28. The computer 28 uses the measured magnetic field values to determine the probe's location and orientation by making comparisons to magnetic field values from a physical model as described below.

The physical model is a set of physical equations that determine values of magnetic fluxes measured by the probe 12 as a function of several parameters. The parameters include positions, orientations, and magnetic moments of field sources 15–20; location, orientation, and sensitivity of probe 12; and characteristics of electronics module 26. A vector (x,y,z) and a pair of angles ($\phi,\theta$) specify the 3-dimensional location and orientation of the sensor coil 13 of the probe 12. If the probe 12 has multiple non-colinear coils, the parameters may include another angular parameter $\psi$ defining a rotational aspect of the probe 12.

The model may describe each source as a magnetic multipole so that the fields measured by the sensor coil 13 are the associated multipole fields, e.g., dipole or quadrupole fields. Those of skill in the art know physical models that describe magnetic dipole or quadrupole fields. The multipole field values depend on the location, orientation and magnetic moment "m" of each source 15–20. The measured values of the magnetic flux depend on the location, size and orientation of the sensor coil 13 with respect to the field sources 15–20.

The physical model is also based on underlying assumptions about the environment near the volume 14. For example, the model assumes preselected values for the locations and orientations of each field source 15–20 and the absence of other sources or field distorting objects. The presence of field distorting objects 30, 32, e.g., conductors or new field sources, may invalidate the models predictions for field values. Of course, the effects of constant background fields may be eliminated, because the sensing coil 13 measures time varying magnetic fields.

Figure 3:
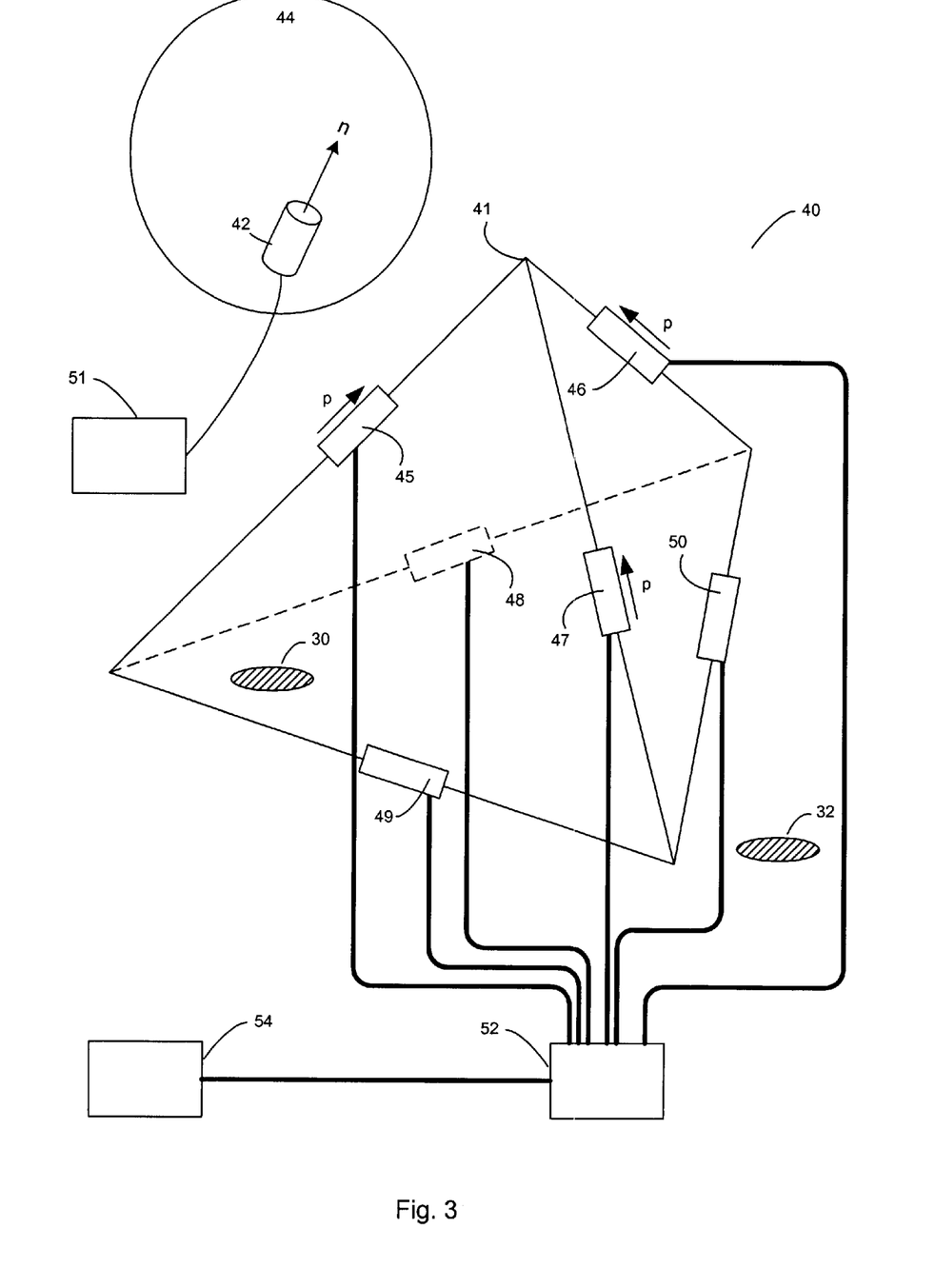
FIG. 3 is a side view of an alternate system that uses magnetic measurements to find a probe's location and orientation.

FIG. 3 shows another system 40 that uses magnetic measurements to find the location and orientation of a moveable probe 42. In the system 40, the roles of the field sensors and sources are interchanged. The movable probe 42, which is located inside an observation volume 44, is a source of a magnetic field, e.g., a time-dependent or a time multiplexed field, and external field sensors 45–50 measure the magnetic field produced by the probe 42. The probe 42 connects to a field-generating module 51, e.g., a voltage source. The field sensors 45–50 are located on edges of a tetrahedron 41 and measure either magnetic fields or magnetic field gradients through induced EMF's. Each sensor 45–50 may have one or more magnetic field sensors oriented to measure fields in various directions. Each sensor 45–50 has an orientation "p" fixed by the orientation of its one or more internal magnetic field sensors.

In other embodiments, the locations, orientations, and number of sensors 45–50 may be different.

An electronics module 52 monitors EMF's from the various field sensors 45–50. The electronics module 52 measures induced EMF's to find magnetic field values. The measured field values are sent to a computer 54, which calculates the location and orientation of the probe 42 from the measured values of the magnetic fields.

Referring to FIGS. 1–3, both systems 10, 40 measure a set of magnetic fluxes to obtain a set of measured magnetic field values $\{B_i^{measured}\}$. The set of measured field values $\{B_i^{measured}\}$ carry an index "i", which distinguishes different measured field values associated with one probe location and orientation. The index "i" has six values for the systems 10 and 40, but other embodiments measure different numbers of magnetic field values.

The set of the measured field values $\{B_i^{measured}\}$, which are obtained from measured magnetic fluxes, also has a non-linear dependence on the 3-dimensional location and orientation of the probe. The probe's location and orientation are defined by a vector (x,y,z) and a pair of azimuthal and polar angles ($\phi,\theta$), respectively. By using a physical model for the "measured" field dependencies, the systems 10, 40 can iteratively determine the probe's location and orientation from the associated set of measured field values $\{B_i^{measured}\}$.

The physical model describes a preselected magnetic environment in the region of the field sensor[s], e.g., the volumes 14 and 44 shown in FIGS. 1 and 3. The preselected magnetic environment may or may not include contributions from nearby conducting objects, i.e., objects 30 and 32. If the preselected environment is different from the actual environment, the model may predict incorrect magnetic field values. The actual environment may be different due to the presence of field distorting objects 30, 32. Field distorting objects 30, 32 include conducting objects that support Eddy currents, e.g., a pair of surgical scissors, ferromagnetic materials, and active sources of magnetic fields. The presence of such objects can invalidate magnetic determinations of the probe's location and orientation.

The iterative process may also yield incorrect probe locations and orientations because of hardware or software failures in modules 22, 26, 51, 52 or computers 28, 54.

The presence of distorting conditions may not be evident to users of the systems 10, 40. The users may be unskilled with respect to physical basis for the magnetic location systems, e.g., the users may be medical doctors. To avoid errors by unskilled users, each system 10, 40 detects and warns users about the presence of potentially measurement distorting conditions, e.g., by flashing messages on a video monitor or through audio alert signals.

Figure 4:
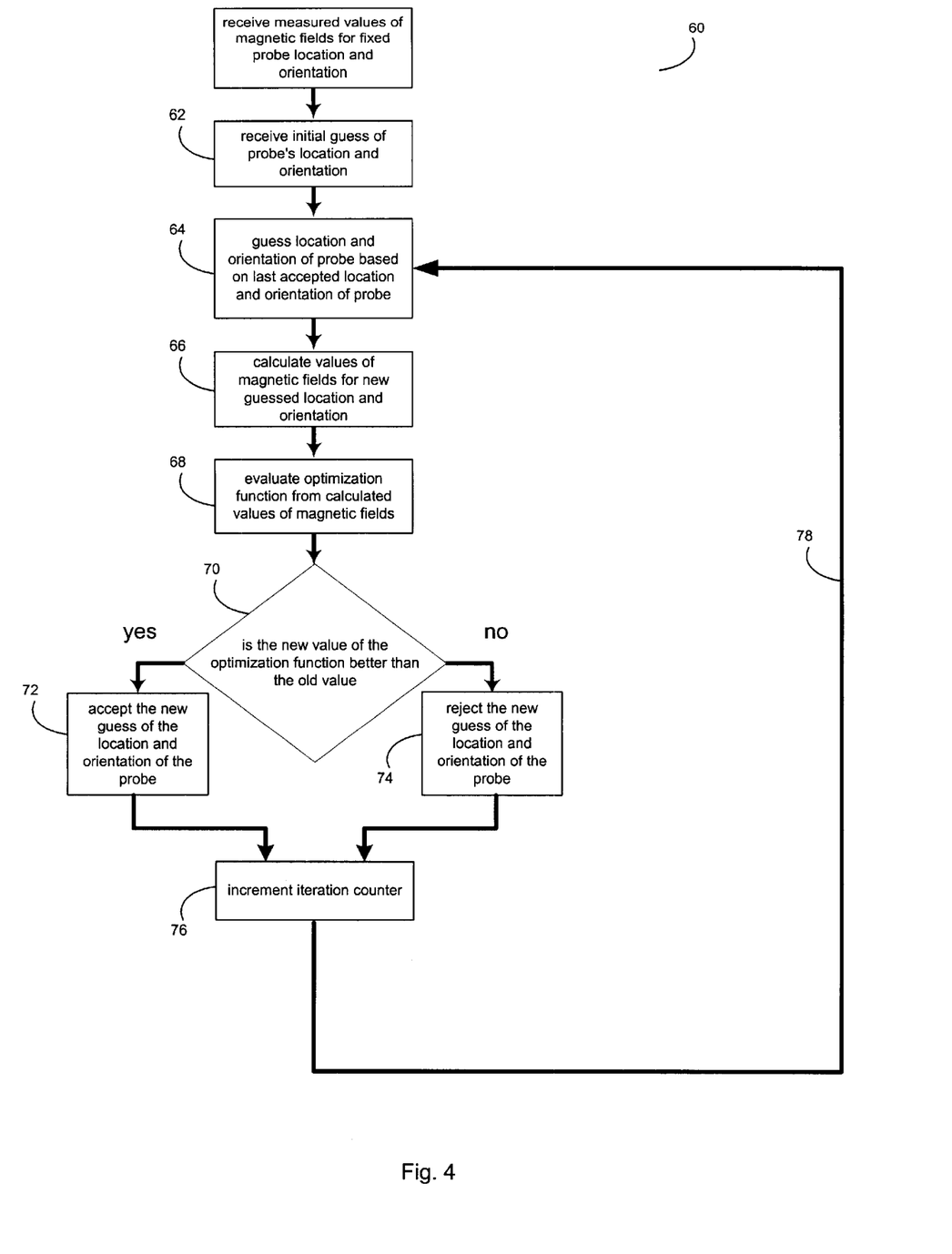
FIG. 4 is a flow chart for a process that iteratively guesses the location and orientation of a probe from measured magnetic field values.

FIG. 4 shows a flow chart for an iterative process 60 to determine a probe's location and orientation. The process 60 uses measured magnetic field values $\{B_i^{measured}\}$, to direct the determination of the probe's location and orientation. From the measured magnet field values, the process 60 can determine the location and orientation of either probe 12 of FIGS. 1–2 or probe 42 of FIG. 3.

The process 60 receives an initial guess for the probe's location and orientation (step 62). The initial guess is a preselected point of the $(x,y,z;\phi,\theta)$ parameter space that defines the location and orientation of the probe. The initial guess is the first accepted guess for the probe's location and orientation. From the last accepted guess, the process makes a new guess for the probe's location and orientation (step 64).

Each new guess of the probe's location and orientation is found from the last accepted guessed by a procedure. The procedure may use a process of Levenberg-Marquardt, a neural network, simulated annealing, a genetic algorithm, or a simplex process.

The process of Levenberg-Marquardt is known to persons of skill in the art as an iterative process to find a best match between a set of measurements and a set of values obtained from preselected nonlinear model equations. The Levenberg-Marquardt process is described in: Numerical Recipes in C: the Art of Scientific Computing, by W. H. Press et al., Cambridge University Press 1992.

Here, the model equations are the set of physical equations $B_i=B_i(x,y,z;\phi,\theta)$, which define the magnetic field values, $B_i$, in terms of the probe's location and orientation coordinates $(x,y,z;\phi,\theta)$. The model equations come from the physical laws of electrodynamics. In one embodiment, the model equations may describe the magnetic field of each field source as a magnetic dipole or as a magnetic quadrupole.

The Levenberg-Marquardt procedure iteratively tries to find a best match between the measured magnetic field values, $B_i^{measured}$, and the magnetic field values, $B_i$, predicted from the physical model equations. The N-th accepted guess for a match is associated with probe location and orientation coordinates $(x_N,y_N,z_N;\phi_N,\theta_N)$. From these coordinates and the physical model equations, the Levenberg-Marquardt process generates an (N+1)-th guess for a match, $B_i$, and associated location and orientation coordinates $(x_{N+1},y_{N+1},z_{N+1};\phi_{N+1},\theta_{N+1})$. The Levenberg-Marquardt equation for the (N+1)-th guess involves the values of the fields, $B_i$, and derivatives of the fields, $B_i$, evaluated at the value of the N-th accepted guess for a match. The Levenberg-Marquardt process provides new guesses that rapidly produce the best match between measured field values, $B_i^{measured}$, and field values, $B_i$, which are obtained from the non-linear model equations.

The process 60 evaluates the quality of each new guess for the probe's location and orientation. To determine the quality, process 60 calculates new magnetic field values corresponding to the new guess for the probe location and orientation, i.e., $B_i^{new}=B_i(x_{N+1},y_{N+1},z_{N+1};\phi_{N+1},\theta_{N+1})$ for the (N+1)-th guess (step 66). Using, both the calculated and the measured magnetic field values, the process 60 evaluates an optimization function (step 68). The optimization function is also referred to as an error function, because the optimization function is sensitive to differences between measured and calculated field values. A global extremum of the optimization function defines the "best" guess for the location and orientation of the probe.

One embodiment uses a least-squares sum, i.e., $\chi^2$, as the optimization function. The extrema of the least-squares sum are minima. The value of the least-squares sum, $\chi^2$ (N), for the magnetic field associated with the N-th guess has the form:

$$\chi^2(N)=\Sigma_i[B_i^{measured}-B_i(x_N, y_N, z_N;\phi_N,\theta_N)]^2/\sigma_i^{\ 2}.$$

sum goes over the "i" members in the set of measured field values, $B_i^{measured}$, which are obtained for a single probe location and orientation. The $\Sigma_i$'s are uncertainties associated with measurements of the $B_i^{measured}$'s.

The process 60 determines whether the value of the optimization function for the new guess is closer to a value at an extremum than the value for the last accepted guess (step 70). For the least-squares sum, the extrema are minima, and the new value is closer to a minimum if $\chi^2(N+1)<\chi^2(N)$. If the value of the optimization function for the new guess is closer to an extremum, the process 60 accepts the new guess for the location and orientation of the probe (step 72). If the value of the optimization function for the new guess is farther from an extremum, e.g., $\chi^2$ (N+1)>$\chi^2$(N), the process 60 rejects the new guess (step 74). After accepting or rejecting the new guess for the probe's location and orientation, the process 60 increments a counter for the number of iterations performed (step 76). Then, the process 60 loops back 78 to find a new and better guess of the probe's location and orientation.

The process 60 outputs the last accepted guess for the probe's location and orientation and a count for the number of iterations, which have been performed. In some embodiments, the process 60 performs a preselected number of iterative loops 78 to find a better guess before reporting the accepted guess for the probe's location and orientation. This produces reported guesses that are closer to values associated with extremum of the optimization function.

Figure 5:
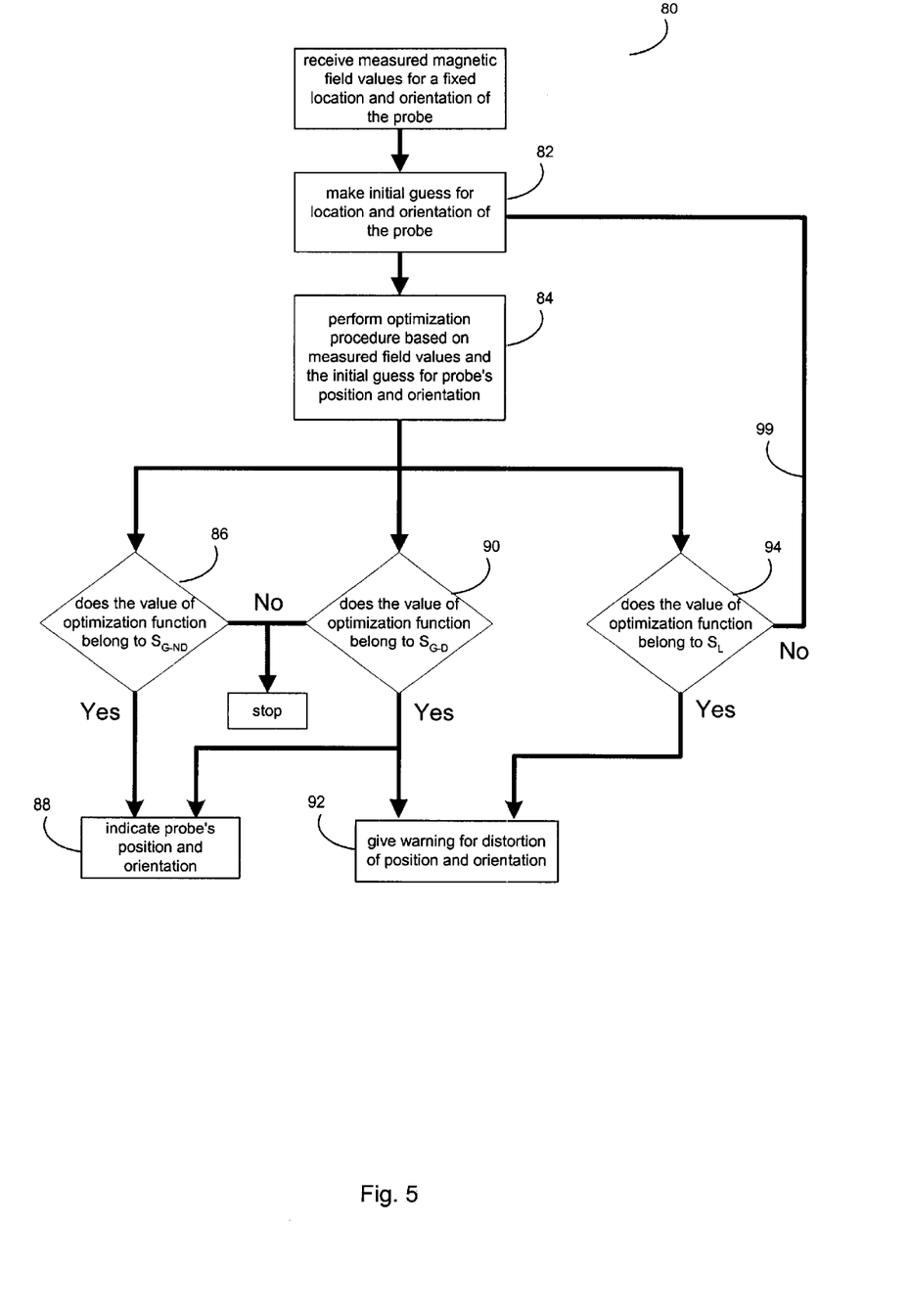
FIG. 5 is a flow chart for a process that determines whether the best guess to the location and orientation of a probe is reliable.

FIG. 5 is a flow chart for a process 80 that uses magnetic field measurements to determine a probe's location and orientation. The process 80 provides an initial guess for the probe's location and orientation (step 82). The initial guess may be either a preselected fixed point or a randomly selected point in the $(x,y,z;\phi,\theta)$ space of probe locations and orientations. For the selected initial guess, the process 80 performs the iterative process 60 of FIG. 4 to obtain a "better" guess to the probe's location and orientation (step 84). The "better" guess is based on the selected initial guess and the measured magnetic field values. The process 80 may perform several iterative loops of the process 60 to obtain a "better" guess, which is closer to an extremum of the optimization function used in the process 60. The optimization process 60 provides a value for the optimization function, e.g., the $\chi^2$-function, and a loop count, which indicates the number of iterations performed to obtain the "better" guess.

The value of the optimization function provides data on the reliability of the better guess to the probe's location and orientation. Random measurement errors cause the value of the optimization function to fall on a probabilistic distribution function whose form is independent of the physical model for the magnetic field measurements. For the least-squares sum, the probabilistic distribution function is known as the $\chi^2$-distribution. Systematic measurement errors also affect the value of the optimization function.

The extrema of the optimization function can be maxima or minima and can fall into several classes. An extremum may be local or global extremum. Local and global extrema are distinguished by the associated values of the optimization function. For the least-squares sum, the value of the optimization function at a global minimum is smaller than the value of the function at a local minimum. Thus, global and local minima are associated with respective low and high values of the least-squares sum.

An extremum may also correspond a situation in which measurements of magnetic fields are either distorted or undistorted. For the least squares sum, values of the optimization function at global minima for undistorted measurements are smaller than values of the optimization function at global minima for distorted measurements. Also, values of the optimization function at global minima for distorted measurements are smaller than values of the optimization function at local minima.

Thus, values of the optimization function at extrema carry information on estimates of a probe's location and orientation obtained through process 60. The information enables determining whether random or systematic errors are present. Values of the least-squares sum at extrema are typically ordered. The lowest values correspond to global minima in the absence of distortions to field measurements. Intermediate values correspond to global minima in the presence of distortions to field measurements. The highest values correspond to false or local minima for which estimates of the probe's location and position are not reliable.

Distortions may occur during generation of magnetic fields, measurement of magnetic fields, acquisition of field measurements, or processing of field measurements. The distortions to the generation of magnetic fields may occur due to a failure of a field source, e.g., sources 15–20 or probe 42, or a field-generating module, e.g., modules 22 or 51. The distortions to magnetic field measurements may result from the presence of conductors or ferromagnetic materials, which distort time-varying magnetic fields, near the measurement system. The distortions to acquisition or processing of magnetic field measurements may result from hardware or software failures, e.g., in the electronics modules 26, 53 or the computers 28, 54, shown in FIGS. 1 and 3.

Prior to performing process 80, a calibration is performed to classify extrema of the optimization function. The calibration classifies extrema of the optimization function into three or more sets, $S_i$. One set, $S_{G-ND}$, corresponds to real global extrema of the optimization function for which field measurements and field measurement processing is not distorted. Another set, $S_L$, corresponds to false or local extrema of the optimization function. A third set, $S_{G-D}$, corresponds to real global extrema of the optimization function for which either field measurements or field measurement processing is distorted.

New sets may be formed from the sets $S_{G-ND}$, $S_L$, and $S_{G-D}$ by set intersection and union operations. One set, $S_{ND}$, includes values of the optimization function that are only associated with global extrema of the function for which field measurements and measurement processing are not distorted. This set is $S_{ND}=S_{G-ND}-(S_L \cup S_{G-ND})$. Another set, $S_D$, includes values of the optimization function that are only associated with global extrema of the function for which field measurements or field measurement processing is distorted. This set is defined by $S_D=S_{G-D}-(S_L \cup S_{G-ND})$. Another set, $S_{L0}$, includes values of the optimization function that are only associated with false or local extrema of the function. This set is defined by $S_{L0}=S_L-(S_{G-ND} \cup S_{G-D})$. Finally, a set, $S_{ND-D}$, includes values of the optimization function that are only associated with global extrema of the function. For values in $S_{ND-D}$, the field measurements and field measurement processing may or may not be distorted. This set is defined by $S_{ND-D}=S_{G-ND} \cup S_{G-D}$.

In various embodiments, some of the above-described sets, $S_i$, may be empty.

Referring again to FIG. 5, the process 80 uses the calibrated classification of values of the optimization function to classify extrema found with the iterative process 60. The process 80 determines whether the value of the optimization function at each extremum corresponds only to a global minimum without distortion (step 86), i.e., whether the value belongs to $S_{G-ND}$. If the value belongs to set $S_{G-ND}$, the process 80 registers the associated "better" guess for the probe's location and orientation as the probe's location and orientation (step 88). For example, the "better" guess for the coordinates $(x,y,z;\phi,\theta)$ may be displayed on a computer screen for a user to view as the final estimate to the location and orientation of the probe.

The process 80 determines whether the value of the optimization function for the "better" guess corresponds to a global extremum in the presence of a distortion (step 90), i.e., whether the value belongs to $S_{G-D}$. If the value belongs to set $S_{G-D}$, the process 80 provides a warning to the user (step 92) and also registers the new guess for the probe's location and orientation for the viewer to see (step 88). For example, the warning may be audio or a flashing signal on a computer display for a user to hear or view.

The process 80 also determines whether the value of the optimization function corresponds to a local extremum, i.e., whether the value belongs to $S_L$ (step 94). If the value belongs to $S_L$, the process 80 determines whether the loop count (LC) is greater than a preselected timeout value ($LC_{max}$) (step 96). If LC>$LC_{max}$, the process 80 generates a timeout warning (step 98). If LC≦$LC_{max}$, the process 80 loops back 99 to generate a better new guess for the probe's location and orientation, i.e., ignoring the current new guess. In the loop back 99, the process 80 selects a new initial guess for the probe's location and orientation, e.g., by randomly selecting a new point in the probe's $(x,y,z;\phi,\theta)$ coordinate space. Other processes for selecting the new initial guess so that the process 60 subsequently produces a better guess for a "global" extremum are known to persons of skill in the art.

In some embodiments, process 80 tries to obtain a better guess for the location and position of the probe after producing a warning that a distortion is present. For example, if the number of field measurements is greater than the number of parameters plus one, the process 80 may produce a better guess by discarding one of the measured field values, $B_i^{measured}$, and repeating process 80. If the distortion affects only the discarded field value, discarding the distorted value will produce a better estimate of the probe's location and orientation through to process 80. One field measurement may be distorted because of the presence of a conductor near one field sensor or because of a hardware failure in one sensor.

Some embodiments of process 80 handle overlapping extreme values, which belong to more than one of the sets of $S_L$, $S_{G-ND}$, and $S_{G-D}$, differently. For extreme values in both $S_L$ and $S_{G-D}$, the process may give a warning (step 90), indicate the guessed probe location and orientation (step 88), and try to find a non-overlapping extreme value by repeating steps 82 and 84 for a new initial guess of the probe's location and orientation. For extreme values belonging to $S_L$–$S_{LO}$, the process may generate a warning that identifies the extreme value as overlapping and then reselect an initial guess for the probe's location and orientation and re-execute process 60 to try to find a value not belonging to $S_L$–$S_{LO}$. Of course, overlapping subsets such as $S_L$–$S_{LO}$ may also be empty.

CALIBRATION OF MAGNETIC LOCATION SYSTEMS

Figure 6:
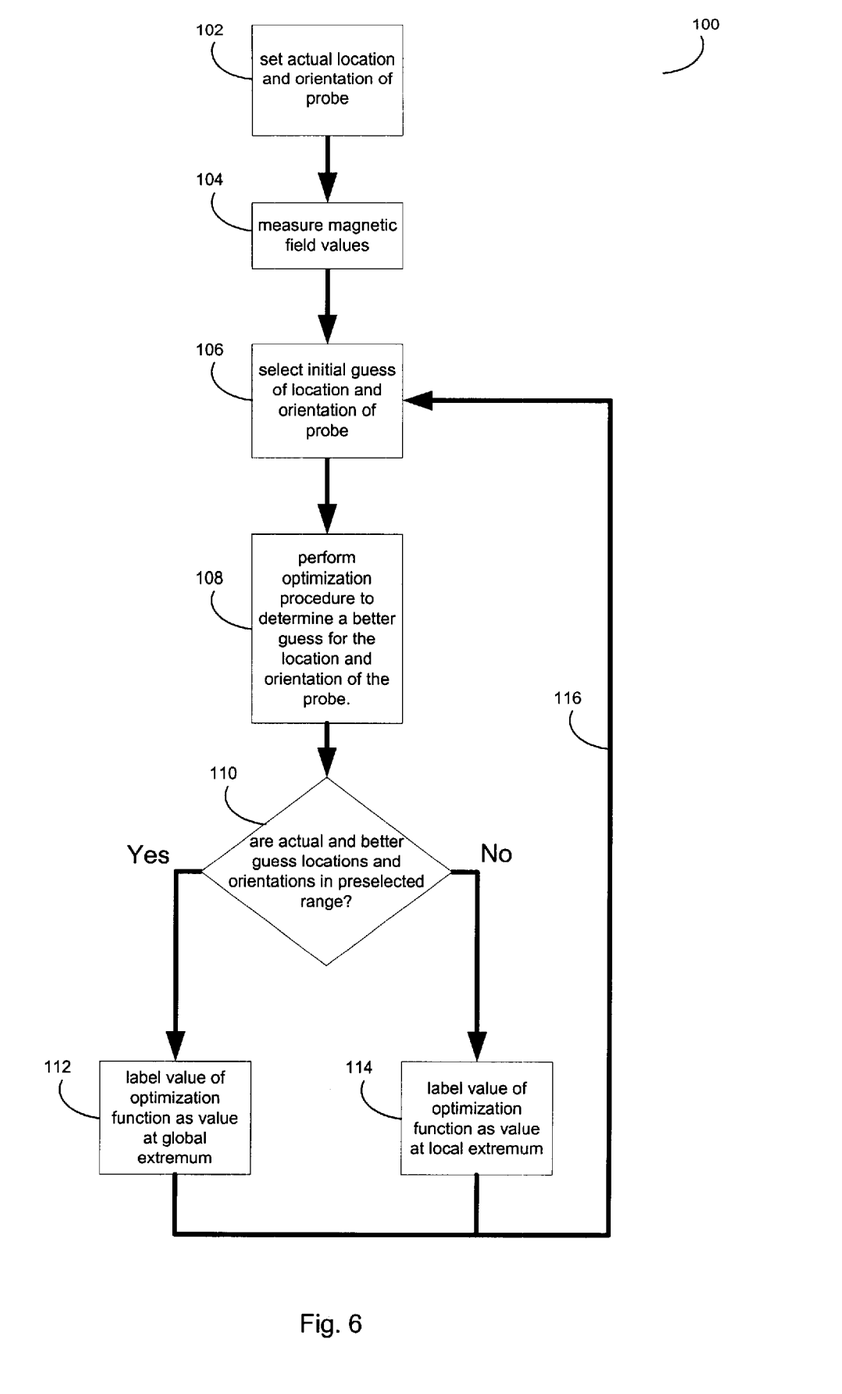
FIG. 6 is a flow chart for a process that evaluates an error or optimization function at global and local extrema.

FIG. 6 is a flow chart for a calibration process 100 that finds values of the optimization function at extrema to define the membership of sets $S_{G-ND}$ and $S_L$. If the iterative process 60 of FIG. 4 generates a real global extremum, the probe location and orientation found by the process 60 correlate closely to the actual location and orientation of the probe. If the iterative processes 60 FIG. 4 generates at a false or local extremum of the optimization function, the probe location and orientation found by the process 60 does not correlate closely to the actual location and orientation of the probe.

To perform the calibration, process 100 positions the probe at a selected location and orientation (step 102). During calibration, the probe mounts on a mechanical positioning frame (not shown) that performs movements to position the probe with the selected location and orientation. The mechanical positioning frame is made of materials that do not distort magnetic fields and provides a separate measurement of the selected actual location and orientation of the probe. The separate measurements may be optical measurements or mechanical measurements. The process 100 measures the set of magnetic field values corresponding to the selected probe location and orientation (step 104).

The process 100 selects an initial guess of the location and position of the probe for the optimization process 60 (step 106). From the measured field values and initial guess, the process 100 performs the iterative optimization procedure 60 of FIG. 4 to obtain a better-guess value of the probe location and orientation (step 108). The optimization procedure 60 also provides a value for the optimization function that corresponds to the better guess for the probe location and orientation and is a value of the optimization function at an extremum.

Process 100 compares the better-guess and actual coordinates of the probe location and orientation to determine whether both coordinates correspond to close points (step 110). The better guess, $(x_N, y_N, z_N; \phi_N, \theta_N)$, and actual values, $(x, y, z; \phi, \theta)$, of the probe coordinates are close if the values are within a preselected range of each other in a component-by-component fashion. If the better-guess and actual coordinates are close, the process 100 labels the corresponding value of the optimization function as a value belonging to $S_{G-ND}$ (step 112). If the better-guess and actual probe coordinates are not close, the process 100 labels the corresponding value of the optimization function as a value belonging to $S_L$ (step 114).

To classify values of the optimization function at each extremum, the process 100 loops back 116 and repeats steps 106–114 for other initial guesses of the probe's location and orientation. These repetitions for different initial guesses cover the whole space $(x, y, z; \phi, \theta)$ of possible probe coordinates uniformly, e.g., by randomly selected points in the $(x, y, z; \phi, \theta)$ space.

The process 100 also repeats the classification of values of the optimization function at extrema for other selections of the actual probe location and orientation. The repetitions for other actual probe locations and orientations cover a representative portion of the parameter space $(x, y, z; \phi, \theta)$ uniformly, e.g., with randomly selected points. The representative portion may be a portion of the entire space $(x, y, z; \phi, \theta)$ that is related to other portions of the space by symmetry rotations.

These repetitions may generate different extreme values of the optimization function that belong to $S_{G-ND}$ and/or $S_L$. For the least-squares sum, the optimization function has smaller values at global minima, i.e., in the presence or absence of measurement distortions, than at local minima.

Figure 7:
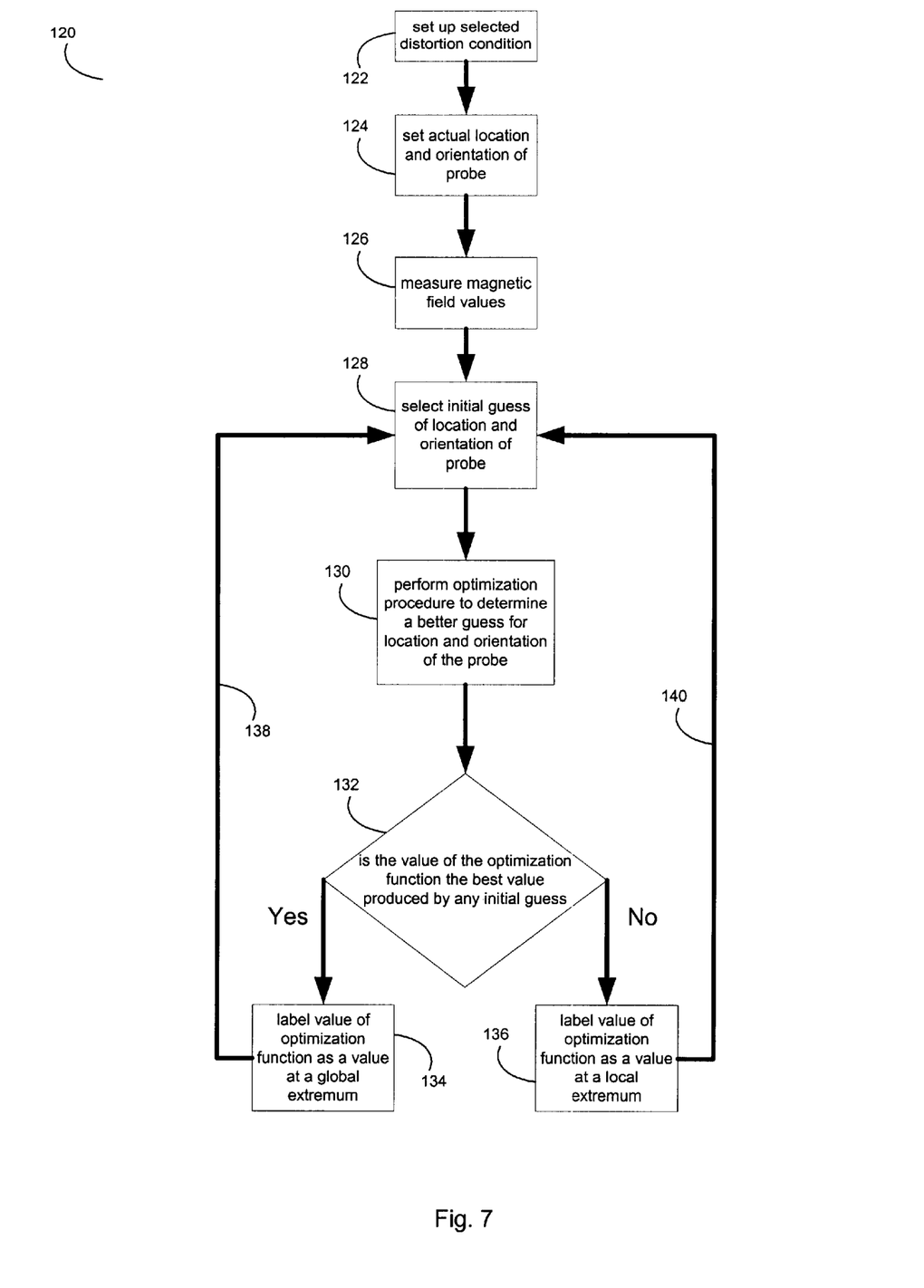
FIG. 7 is a flow chart for a process that determines extreme values of the error or optimization function that correspond to the presence of distortions.

FIG. 7 is a flow chart for a calibration process 120 that finds values of the optimization function belonging to $S_{G-D}$. The values of $S_{G-D}$ correspond to extrema of the optimization function that occur when distortions affect the process 60 of FIG. 4. The process 120 may be performed separately for each type of distortion that can affect either magnetic field measurements or the processing of magnetic field measurements. The distortions may result from nearby conducting or ferrous objects, nearby field sources, sensor hardware failures, field source hardware/software failures, and/or software measurement processing failures.

The process 120 physically sets up a selected type of distortion for system 10 or 40 (step 122). For example, the setting up of a distortion may include placing a pair of conducting scissors inside volume 14, shown in FIG. 1, or causing a hardware failure in the electronics module 26. After setting up the distortion condition, the process 120 positions the probe with the mechanical positioning frame and receives the value of the probe's actual location and orientation (step 124). The process also measures magnetic field values $B_i$'s, which depend on the probe's actual location and orientation (step 126). The process 120 also selects an initial guess for the location and orientation of the probe (step 128).

From the measured field values and selected initial guess, the process 120 uses the iterative process 60 of FIG. 4 to obtain a better guess for the probe's location and orientation (step 130). The iterative process 60 returns an associated extreme value of the optimization function that corresponds to each better guess. The process 120 determines whether the new value is better than other extreme values of the optimization function, which were generated from different initial guesses for the probe's location and position (step 132). For the least-squares sum, the best extreme value is the minimum value.

If the new value is better than values associated with earlier accepted guesses, the process 120 labels the new value as a value of the optimization function at a global extremum, i.e., as a member of $S_{G-D}$ (step 134). Values of the optimization function that belong to $S_{G-D}$ indicate the presence of a distortion. If the new value is not better than earlier values of the optimization function associated with accepted guesses, the process 120 ignores the new value as a value that corresponds to a false or local extremum (step 136). After classifying the extreme value, the process 120 loops back 138, 140 to repeat the search for values of the optimization function at other extrema by selecting a different initial guess for the probe's location and orientation. The best extreme value for various initial guesses of the probe's location and orientation provides a value in $S_{G-D}$.

The process also repeats the search for values of the optimization function in $S_{G-D}$ for different actual locations and orientations of the probe. For each actual orientation and location an extreme value of the optimization function in $S_{G-D}$ may be generated. Similarly, different positions of a distorting object, e.g., objects 30 and 32 of FIG. 1, may generate different extreme values of the optimization function, which belong to $S_{G-D}$.

In some embodiments, the extreme values of the optimization function for different types of distortion are distinguishable. Distinguishable extreme values fall in different ranges. In such embodiments, the calibration process 120 is performed separately for the different types of distortion to obtain ranges of extreme values of the optimization function for each separate type of distortion. The process 80 of FIG. 5 uses the extreme values to classify the type of distortion, e.g., hardware failure, software failure, or nearby conducting object.

Figure 8:
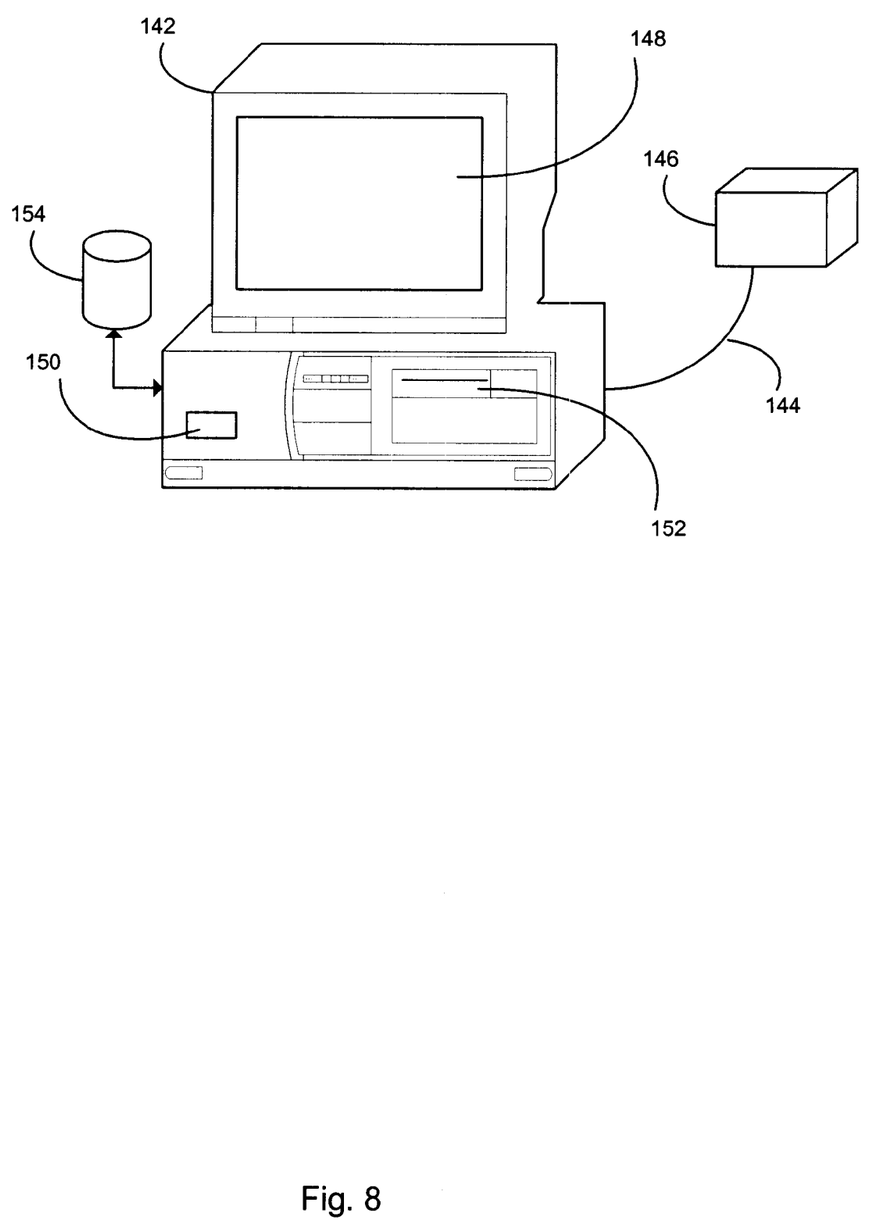
FIG. 8 shows a computer that finds a probe's location and orientation from measurements of magnetic fields.

FIG. 8 shows a computer 142 that determines locations and orientations of a probe from measurements of magnetic fields and indicates the presence of distortions to the determinations. The computer 142 may be an embodiment for the computer 28 of FIG. 1 or the computer 54 of FIG. 3.

The computer 142 receives data on measured magnetic field values from a line 144 that connects to an output of an electronics module 146. The module 146 may be module 26 or module 52 of FIG. 1 and FIG. 3, respectively. The computer 142 processes the data according to processes 60 and 80 of FIGS. 4 and 5 to determine a probe's location and orientation and the presence or absence of distortions to the determination. The computer 142 displays results of the determinations on a screen 148.

The computer 142 has an active storage medium 150 for storing executable programs and data and a drive 152 for reading executable programs from a storage medium 154, e.g., a magnetic or optical disk. The media 150 and 152 can store a program of instructions for execution by computer 142 of processes 60 and 80.

Other embodiments are within the scope of the following claims.

What is claimed is:

1. A process for detecting distortions to probe location or orientation determinations, comprising:
   measuring a plurality of magnetic field values, the measured values depending on a probe's location and a probe's orientation;
   determining one of the probe's location and the probe's orientation from an extremum of an optimization function, the function depending on differences between the measured field values and field values from a model, determining one of the probe's location and the probe's orientation includes:
   guessing a location and orientation of the probe,
   calculating magnetic field values associated with the guessed location and orientation from a model, and
   evaluating a new value of the optimization function from the calculated and measured values;
   rejecting the guessed location and orientation in response to the new value being farther from an extremum of the function than an earlier calculated value of the function; and
   indicating that a distortion to the determining exists in response to the extremum belonging to a preselected range of values associated with presence of distortion.

2. The process of claim 1, further comprising:
   providing a predicted value for one of the probe's location and the probe's orientation in response to the extremum belonging to another preselected range of values.

3. The process of claim 2, reperforming the determining to find another extremum in response to the extremum not corresponding to a global extremum of the function.

4. The process of claim 2, wherein values of the preselected ranges correspond to global extrema of the function.

5. The process of claim 2, wherein the optimization function is a least-squares sum of the measured field values and calculated field values.

6. The process of claim 2, wherein the another preselected range corresponds to a global minimum of the optimization function.

7. The process of claim 2, wherein the preselected range includes a value corresponding to a global minima of the least-squares function.

8. The process of claim 1, wherein the act of indicating is responsive to presence of a passive distortion to the measured magnetic field by one of a nearby conductor and a ferromagnetic object.

9. The process of claim 1, wherein the act of indicating is responsive to presence of a active distortion to the measured magnetic field by a nearby field source.

10. The process of claim 1, wherein the act of indicating is responsive to presence of a malfunction of one of hardware and software that processes data from a field sensor.

11. The process of claim 1, wherein the act of indicating is responsive to presence of a malfunction of one of hardware and software that controls a field source.

12. The process of claim 1, further comprising:
    discarding one of the measured field values; and
    redetermining one of the probe's location and the probe's orientation from remaining measured field values in response to finding that a distortion is present.

13. A program storage medium storing computer executable instructions, the instructions to cause a computer to:
    receive data representative of measured magnetic field values that depend on a probe's location and orientation;
    determine one of the probe's location and the probe's orientation from an extremum of an optimization function, the function depending on differences between the measured field values and field values from a model, determine one of the probe's location and the probe's orientation includes:
    guess a location and orientation of the probe,
    calculate magnetic field values associated with the guessed location and orientation from a model, and
    evaluate a new value of the optimization function from the calculated and measured values;
    reject the guessed location and orientation in response to the new value being farther from an extremum of the function than an earlier calculated value of the function;
    indicate that a distortion to the determining exists in response to the extremum belonging to a preselected range associated with presence of distortion; and
    provide a predicted value for one of the probe's location and the probe's orientation in response to the extremum belonging to another preselected range of values.

14. The medium of claim 13, the instructions further causing the computer to:

find another extremum of the optimization function in response to a previously found extremum not corresponding to a global extremum of the function.

15. The medium of claim 13, wherein values of the preselected sets correspond to global extrema of the function.

16. The medium of claim 13, wherein the optimization function is a least-squares sum of the measured field values and calculated field values.

17. The medium of claim 16, wherein the another preselected range corresponds to a global minimum of the least-squares function.

18. The medium of claim 13, wherein the preselected range includes a value corresponding to a global extremum of the optimization function.

19. The medium of claim 13, wherein the instructions causing the computer to indicate are responsive to presence of a distortion to the measured magnetic field by one of a nearby conductor and a ferromagnetic object.

20. The medium of claim 13, wherein the instructions causing the computer to indicate are responsive to presence of a malfunction of one of hardware and software that processes data from a field sensor.

21. A process for detecting distortions to probe location or orientation determinations, comprising:
    determining a preselected range of values associated with the presence of a certain condition;
    measuring a plurality of magnetic field values, the measured values depending on a probe's location and a probe's orientation;
    determining one of the probe's location and the probe's orientation from an extremum of an optimization function, the function depending on differences between the measured field values and field values from a model; and
    indicating that a distortion to the determining exists in response to the extremum belonging to the preselected range of values associated with presence of a certain condition;
    wherein determining a preselected range includes:
        setting up a condition that distorts determinations of the probe's location and the probe's orientation from measured fields,
        determining an actual probe location and orientation,
        measuring magnetic field values depending on the location and orientation,
        finding an extremum of an optimization function that depends on differences between the measured field values and field values calculated from a model and guessed probe location and position, and
        assigning the extremum to the preselected range of values associated with the presence of the certain condition.

22. The process of claim 21, further comprising:
    rejecting the extremum in response to the extremum being a local extremum.

23. The process of claim 21, wherein the finding comprises:
    selecting an initial guess for the probe's location and the probe's orientation;
    calculating magnetic field values associated with the initial guess from the model; and
    evaluating a new value of the optimization function from the calculated and measured magnetic field values.

24. The process of claim 21, wherein the condition is a failure of one of an electronics module and software that processes data on magnetic field values received from one or more field sensors.

25. The process of claim 21, wherein the condition is a presence of a source of a magnetic field absent from the model.

26. The process of claim 21, wherein the condition is a presence of one of a conductive object and a ferromagnetic object.

27. The process of claim 21, further comprising repeating the acts of setting up a condition, determining, measuring, finding, and assigning for a second type of condition.

* * * * *